(12) United States Patent
Nantermet et al.

(10) Patent No.: US 7,348,448 B2
(45) Date of Patent: Mar. 25, 2008

(54) PHENYLCARBOXYLATE BETA-SECRETASE INHIBITORS FOR THE TREATMENT OF ALZHEIMER'S DISEASE

(75) Inventors: Philippe G. Nantermet, Lansdale, PA (US); Hemaka Anthony Rajapakse, Wyncote, PA (US); Harold G. Selnick, Ambler, NJ (US)

(73) Assignee: Merck & Co., Inc., Rahway, NJ (US)

( * ) Notice: Subject to any disclaimer, the term of this patent is extended or adjusted under 35 U.S.C. 154(b) by 122 days.

(21) Appl. No.: 10/562,470

(22) PCT Filed: Jun. 25, 2004

(86) PCT No.: PCT/US2004/020525

§ 371 (c)(1),
(2), (4) Date: Dec. 22, 2005

(87) PCT Pub. No.: WO2005/004803

PCT Pub. Date: Jan. 20, 2005

(65) Prior Publication Data

US 2006/0149092 A1    Jul. 6, 2006

Related U.S. Application Data

(60) Provisional application No. 60/484,150, filed on Jul. 1, 2003.

(51) Int. Cl.
*C07C 313/00* (2006.01)
*C07C 255/00* (2006.01)

(52) U.S. Cl. .................................. 558/61; 558/411

(58) Field of Classification Search ............... 558/61, 558/411
See application file for complete search history.

(56) References Cited

FOREIGN PATENT DOCUMENTS

| | | |
|---|---|---|
| EP | 1 186 305 | 3/2002 |
| JP | 02000129 | 5/1990 |
| WO | WO 89/04833 | 6/1989 |
| WO | WO 01/00665 | 1/2001 |
| WO | WO 03/072535 | 9/2003 |
| WO | WO 03/106405 | 12/2003 |
| WO | WO 2005/053374 | 1/2005 |

OTHER PUBLICATIONS

C. A. Coburn et al., "Identification of a Small Molecule Nonpeptide Active Site Beta-Secretase Inhibitor That Displays a Nontraditional Binding Mode for Aspartyl Proteases," J. Med. Chemistry, vol. 47, pp. 6117-6119 (2004).
E. Rubini et al., "Synthesis of Isosteric Methylene-Oxy Pseudodipeptide Analogues As Novel Amide Bond Surrogate Units," Tetrahedron, vol. 42, No. 21, pp. 6039-6045 (1986).
CAPLUS Abstract 113:40174.
CAPLUS Abstract 139:230480.
CAPLUS Abstract 136:232115.

*Primary Examiner*—Yvonne Eyler
*Assistant Examiner*—Jennifer Y Cho
(74) *Attorney, Agent, or Firm*—William Krovatin; John C. Todaro

(57) ABSTRACT

The present invention is directed to compounds which are inhibitors of the beta-secretase enzyme and that are useful in the treatment of diseases in which the beta-secretase enzyme is involved, such as Alzheimer's disease. The invention is also directed to pharmaceutical compositions comprising these compounds and the use of these compounds and compositions in the prevention or treatment of such diseases in which the beta-secretase enzyme is involved.

13 Claims, No Drawings

PHENYLCARBOXYLATE BETA-SECRETASE INHIBITORS FOR THE TREATMENT OF ALZHEIMER'S DISEASE

CROSS-REFERENCE TO RELATED APPLICATIONS

This application claims priority under 35 U.S.C. § 119(e) from Provisional Application Ser. No. 60/484,150, filed Jul. 1, 2003.

REFERENCE TO JOINT RESEARCH AGREEMENT

This invention was made as a result of activities undertaken within the scope of a Joint Research Agreement between Merck & Co., Inc. and Sunesis Pharmaceuticals, Inc.

BACKGROUND OF THE INVENTION

Alzheimer's disease is characterized by the abnormal deposition of amyloid in the brain in the form of extra-cellular plaques and intra-cellular neurofibrillary tangles. The rate of amyloid accumulation is a combination of the rates of formation, aggregation and egress from the brain. It is generally accepted that the main constituent of amyloid plaques is the 4 kD amyloid protein (βA4, also referred to as Aβ, β-protein and βAP) which is a proteolytic product of a precursor protein of much larger size. The amyloid precursor protein (APP or AβPP) has a receptor-like structure with a large ectodomain, a membrane spanning region and a short cytoplasmic tail. The Aβ domain encompasses parts of both extra-cellular and transmembrane domains of APP, thus its release implies the existence of two distinct proteolytic events to generate its $NH_2$- and COOH-termini. At least two secretory mechanisms exist which release APP from the membrane and generate soluble, COOH-truncated forms of APP ($APP_S$). Proteases that release APP and its fragments from the membrane are termed "secretases." Most $APP_S$ is released by a putative α-secretase which cleaves within the Aβ protein to release α-$APP_S$ and precludes the release of intact Aβ. A minor portion of $APP_S$ is released by a β-secretase ("β-secretase"), which cleaves near the $NH_2$-terminus of APP and produces COOH-terminal fragments (CTFs) which contain the whole Aβ domain.

Thus, the activity of β-secretase or β-site amyloid precursor protein-cleaving enzyme ("BACE") leads to the abnormal cleavage of APP, production Aβ, and accumulation of β amyloid plaques in the brain, which is characteristic of Alzheimer's disease (see R. N. Rosenberg, Arch. Neurol., vol. 59, September 2002, pp. 1367-1368; H. Fukumoto et al, Arch. Neurol., vol. 59, September 2002, pp. 1381-1389; J. T. Huse et al, J. Biol. Chem., vol 277, No. 18, issue of May 3, 2002, pp. 16278-16284; K. C. Chen and W. J. Howe, Biochem. Biophys. Res. Comm, vol. 292, pp 702-708, 2002). Therefore, therapeutic agents that can inhibit β-secretase or BACE may be useful for the treatment of Alzheimer's disease.

The compounds of the present invention are useful for treating Alzheimer's disease by inhibiting the activity of β-secretase or BACE, thus preventing the formation of insoluble Aβ and arresting the production of Aβ.

SUMMARY OF THE INVENTION

The present invention is directed to compounds that are inhibitors of the β-secretase enzyme that are useful in the treatment of diseases in which the β-secretase enzyme is involved, such as Alzheimer's disease. The invention is also directed to pharmaceutical compositions comprising these compounds and the use of these compounds and compositions in the prevention or treatment of such diseases in which the β-secretase enzyme is involved.

DETAILED DESCRIPTION OF THE INVENTION

The present invention is directed to compounds of the formula I:

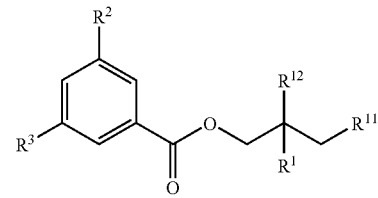

wherein:

$R^1$ is selected from the group consisting of:
(1) —$C_{1-6}$alkyl,
(2) —$C_{2-6}$ alkenyl,
(3) —$C_{2-6}$ alkynyl,
  wherein said alkyl, alkenyl or alykynyl is unsubstituted or substituted with phenyl, which is unsubstituted or substituted with a group selected from:
  (i) halo,
  (ii) —$C_{1-6}$alkyl,
  (iii) —$C_{2-6}$ alkenyl,
  (iv) —$C_{2-6}$ alkynyl,
  (v) —OH, and
  (vi) —O—$C_{1-6}$alkyl, and
(4) hydrogen;

$R^2$ is selected from the group consisting of:
(1) $R^4$—$S(O)_2N(R^7)$—,
  wherein $R^4$ is independently selected from the group consisting of:
  (a) —$C_{1-6}$alkyl,
  (b) —$C_{2-6}$ alkenyl,
  (c) —$C_{2-6}$ alkynyl,
    wherein said alkyl, alkenyl and alkynyl is unsubstituted or substituted with 1-6 fluoro,
  (d) phenyl, and
  (e) benzyl,
  wherein $R^7$ is independently selected from the group consisting of:
  (a) hydrogen,
  (b) —$C_{1-6}$alkyl,
  (c) —$C_{2-6}$ alkenyl, and
  (d) —$C_{2-6}$ alkynyl, or (2)

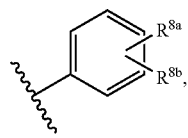

wherein $R^{8a}$ and $R^{8b}$ are independently selected from the group consisting of:
(a) hydrogen,
(b) —CN,
(c) halo,
(d) —$C_{1-6}$alkyl,
(e) —$C_{2-6}$ alkenyl,
(f) —$C_{2-6}$ alkynyl $R^3$ is selected from the group consisting of:

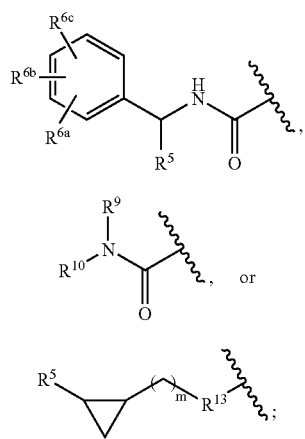

$R^{6a}$, $R^{6b}$, and $R^{6c}$ are independently selected from the group consisting of:
(1) hydrogen, and
(2) halogen;

$R^5$ is selected from the group consisting of:
(1) —$C_{1-6}$alkyl,
(2) —$C_{2-6}$ alkenyl,
(3) —$C_{2-6}$ alkynyl,
wherein said alkyl, alkenyl and alkynyl is unsubstituted or substituted with phenyl, and
(4) hydrogen;

$R^{13}$ is selected from the group consisting of —CH=CH— and —O—;

$R^9$ and $R^{10}$ are independently selected from the group consisting of:
(1) hydrogen,
(2) —$C_{1-6}$alkyl,
(3) —$C_{2-6}$ alkenyl, and
(4) —$C_{2-6}$ alkynyl,
wherein said alkyl, alkenyl and alkynyl is unsubstituted or substituted with phenyl,
or $R^9$ and $R^{10}$ may be joined together to form a pyrrolidine or piperidine ring which is unsubstituted or substituted with $C_{1-6}$alkyl, $C_{1-6}$alkyl-O—$C_{1-6}$alkyl, phenyl or pyridyl;

$R^{11}$ is selected from the group consisting of:
(1) —OH,
(2) —O—$C_{1-6}$alkyl,
(3) —O—$C_{1-6}$alkyl-phenyl,
(4) —O-phenyl, and
(5) phenyl;

$R^{12}$ is selected from the group consisting of:
(1) —$NR^9R^{10}$, and
(2) —OH;

m is independently 0, 1, or 2;

and pharmaceutically acceptable salts thereof.

An embodiment of the present invention is directed to compounds of the formula II:

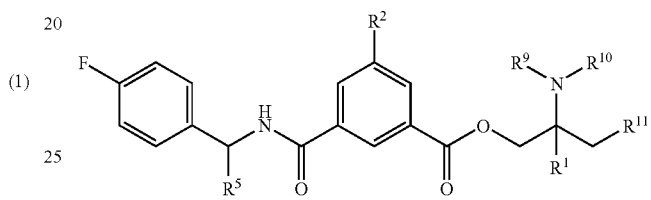

II wherein:

$R^1$ is selected from the group consisting of:
(1) $C_{1-6}$alkyl, unsubstituted or substituted with phenyl, and
(2) hydrogen;

$R^2$ is selected from the group consisting of:
(1) $R^4$—$S(O)_2N(R^7)$—,
wherein $R^4$ is independently selected from the group consisting of:
(a) $C_{1-6}$alkyl, which is unsubstituted or substituted with 1-6 fluoro,
(b) phenyl, and
(c) benzyl,
wherein $R^7$ is independently selected from the group consisting of:
(a) hydrogen, and
(b) —$C_{1-6}$alkyl,
(2)

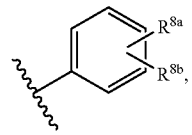

wherein $R^{8a}$ and $R^{8b}$ are independently selected from the group consisting of:
(a) hydrogen,
(b) —CN,
(c) halo, and
(d) —$C_{1-6}$alkyl, $R^5$ is selected from the group consisting of:
(1) $C_{1-6}$alkyl, unsubstituted or substituted with phenyl, and
(2) hydrogen;

$R^9$ and $R^{10}$ are independently selected from the group consisting of:
(1) hydrogen, and
(2) $C_{1-6}$alkyl, unsubstituted or substituted with phenyl;

$R^{11}$ is selected from the group consisting of:
(1) —OH,
(2) —O-phenyl, and
(3) phenyl.

An embodiment of the present invention is directed to compounds of the formula III:

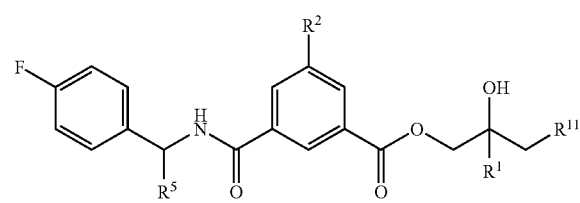

III wherein:

$R^1$ is selected from the group consisting of:
(1) $C_{1-6}$alkyl, unsubstituted or substituted with phenyl, and
(2) hydrogen;

$R^2$ is selected from the group consisting of:
(1) $R^4$—S(O)$_2$N($R^7$)—,
 wherein $R^4$ is independently selected from the group consisting of:
  (a) $C_{1-6}$alkyl, which is unsubstituted or substituted with 1-6 fluoro,
  (b) phenyl, and
  (c) benzyl,
 wherein $R^7$ is independently selected from the group consisting of:
  (a) hydrogen, and
  (b) —$C_{1-6}$alkyl,
(2)

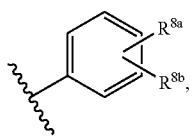

wherein $R^{8a}$ and $R^{8b}$ are independently selected from the group consisting of:
  (a) hydrogen,
  (b) —CN,
  (c) halo, and
  (d) —$C_{1-6}$alkyl, $R^5$ is selected from the group consisting of:
(1) $C_{1-6}$alkyl, unsubstituted or substituted with phenyl, and
(2) hydrogen;

$R^{11}$ is selected from the group consisting of:
(1) —OH,
(2) —O-phenyl, and
(3) phenyl.

In an embodiment of the present invention $R^1$ is selected from the group consisting of:
(1) benzyl,
(2) phenyl-ethyl-,
(3) methyl, and
(4) hydrogen. In another embodiment of the present invention $R^2$ is $CH_3$—S(O)$_2$N(CH$_3$)—.

In another embodiment of the present invention $R^2$ is cyano-phenyl-.

In another embodiment of the present invention $R^5$ is methyl.

In another embodiment of the present invention $R^9$ and $R^{10}$ are independently selected from the group consisting of:
(1) hydrogen, and
(2) methyl.

In another embodiment of the present invention $R^{11}$ is —OH.

Another embodiment of the present invention includes a compound which is selected from the title compounds of the following Examples and pharmaceutically acceptable salts thereof.

The compounds of the instant invention have at least one asymmetric center. Additional asymmetric centers may be present depending upon the nature of the various substituents on the molecule. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of these compounds.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

The compounds of the present invention are prepared by the methods outlined in Scheme 1.

SCHEME 1

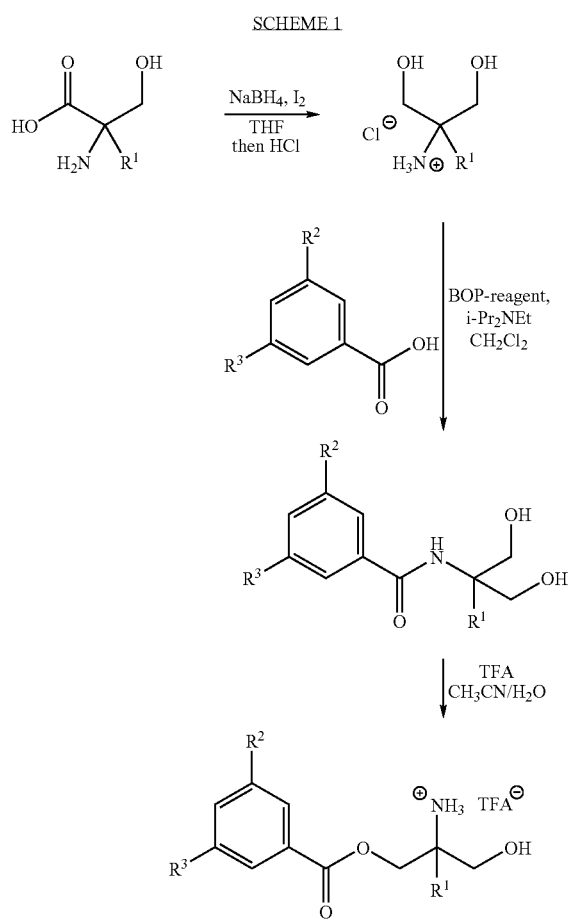

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six carbon atoms. Exemplary alkyl groups include methyl, ethyl, n-propyl, isopropyl, n-butyl, isobutyl, tert-butyl, pentyl, hexyl, and the like.

As used herein, the term "alkenyl," by itself or as part of another substituent, means a straight or branched chain hydrocarbon radical having a single carbon-carbon double bond and the number of carbon atoms designated (e.g., $C_{2-10}$ alkenyl means an alkenyl group having from two to ten carbon atoms). Preferred alkenyl groups for use in the invention are $C_{2-6}$ alkenyl groups, having from two to six carbon atoms. Exemplary alkenyl groups include ethenyl and propenyl.

As used herein, the term "alkynyl" by itself or as part of another substituent, means a straight or branched chain hydrocarbon radical having a single carbon-carbon triple bond and the number of carbon atoms designated (e.g., $C_{2-10}$ alkynyl means an alkynyl group having from two to ten carbon atoms). Preferred alkynyl groups for use in the invention are $C_{2-6}$ alkynyl groups, having from two to si carbon atoms. Exemplary alkynyl groups include ethynyl and propynyl.

The term "substantially pure" means that the isolated material is at least 90% pure, and preferably 95% pure, and even more preferably 99% pure as assayed by analytical techniques known in the art. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids.

The present invention is directed to the use of the compounds disclosed herein as inhibitors of β-secretase enzyme activity or β-site amyloid precursor protein-cleaving enzyme ("BACE") activity, in a patient or subject such as a mammal in need of such inhibition, comprising the administration of an effective amount of the compound. The terms "β-secretase enzyme," "β-site amyloid precursor protein-cleaving enzyme," and "BACE" are used interchangably in this specification. In addition to humans, a variety of other mammals can be treated according to the method of the present invention.

The present invention is further directed to a method for the manufacture of a medicament or a composition for inhibiting β-secretase enzyme activity in humans and animals comprising combining a compound of the present invention with a pharmaceutical carrier or diluent.

The compounds of the present invention have utility in treating, preventing the progression, ameliorating, controlling or reducing the risk of Alzheimer's disease, other diseases mediated by abnormal cleavage of amyloid precursor protein (also referred to as APP), and other conditions that may be treated or prevented by inhibition of β-secretase. Such conditions include mild cognitive impairment, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, Down syndrome, pancreatitis, inclusion body myositis, other peripheral amyloidoses, diabetes and atherosclerosis.

The subject or patient to whom the compounds of the present invention is administered is generally a human being, male or female, in whom inhibition of β-secretase enzyme activity is desired, but may also encompass other mammals, such as dogs, cats, mice, rats, cattle, horses, sheep, rabbits, monkeys, chimpanzees or other apes or primates, for which inhibition of β-secretase enzyme activity or treatment of the above noted disorders is desired.

The compounds of the present invention may be used in combination with one or more other drugs in the treatment, prevention, control, amelioration, or reduction of risk of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention with other drugs in either unit dose or kit form include combinations with: anti-Alzheimer's agents, for example other beta-secretase inhibitors or gamma-secretase inhibitors; HMG-CoA reductase inhibitors; NSAIDs including ibuprofen; vitamin E; anti-amyloid antibodies, including humanized monoclonal antibodies; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil and tacrine; growth hormone secretagogues such as ibutamoren, ibutamoren mesylate, and capromorelin; histamine $H_3$ antagonists; AMPA agonists; PDE IV inhibitors; $GABA_A$ inverse agonists; neuronal nicotinic agonists; or other drugs that affect receptors or enzymes that either increase the efficacy, safety, convenience, or reduce unwanted side effects or toxicity of the compounds of the present invention. The foregoing list of combinations is illustrative only and not intended to be limiting in any way.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by admixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

Compositions for oral use may also be presented as hard gelatin capsules wherein the active ingredient is mixed with an inert solid diluent, or as soft gelatin capsules wherein the active ingredient is mixed with water or an oil medium.

Aqueous suspensions contain the active materials in admixture with excipients suitable for the manufacture of aqueous suspensions. Such excipients include suspending agents, and dispersing or wetting agents. The aqueous suspensions may also contain one or more preservatives, coloring agents, flavoring agents, and sweetening agents.

Oily suspensions may be formulated by suspending the active ingredient in a vegetable oil or in a mineral oil. The oily suspensions may contain a thickening agent. Sweetening agents and flavoring agents may be added to provide a palatable oral preparation. These compositions may be preserved by the addition of an anti-oxidant.

Dispersible powders and granules suitable for preparation of an aqueous suspension by the addition of water provide the active ingredient in admixture with a dispersing or wetting agent, suspending agent and one or more preservatives. Additional excipients, for example sweetening, flavoring and coloring agents, may also be present.

The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, which may be formulated according to the known art, or may be administered in the form of suppositories for rectal administration of the drug.

The compounds of the present invention may also be adminsistered by inhalation, by way of inhalation devices known to those of ordinary skill in the art, or transdermally by way of transdermal patch.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individuals body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

As used herein, the term "treating" means any administration of a compound of athe present invention and includes (1) inhibiting the disease in an animal that is experiencing or displaying the pathology of symptomatology of the disease (i.e., arresting further development of the pathology and/or symptomatology), or (2) ameliorating the disease in an animal that is experiencing or displaying the pathology or symptomatology of the disease (i.e., reversing the pathology and/or symptomatology). The term "controlling" includes preventing treating, eradicating, ameliorating or otherwise reducing the severity of the condition being controlled.

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person adminstering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples in the pharmacy arts of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person adminstering the drug to the patient. Such kits may be provided with all necessary materials and ingredients contained therein, or they may contain instructions for using or making materials or components that must be obtained independently by the patient or person administering the drug to the patient.

When treating, preventing, controlling, ameliorating, or reducing the risk of Alzheimer's disease or other diseases for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. The total daily dosage is from about 1.0 milligrams to about 2000 milligrams, preferably from about 0.1 milligrams to about 20 milligrams per kilogram of body weight. In the case of a 70 kg adult human, the total daily dose will generally be from about 7 milligrams to about 1,400 milligrams. This dosage regimen may be adjusted to provide the optimal therapeutic response. The compounds may be administered on a regimen of 1 to 4 times per day, preferably once or twice per day.

Specific dosages of the compounds of the present invention, or pharmaceutically acceptable salts thereof, for administration include 1 mg, 5 mg, 10 mg, 30 mg, 80 mg, 100 mg, 150 mg, 300 mg and 500 mg. Pharmaceutical compositions of the present invention may be provided in a formulation comprising about 0.5 mg to 1000 mg active ingredient; more preferably comprising about 0.5 mg to 500 mg active ingredient; or 0.5 mg to 250 mg active ingredient; or 1 mg to 100 mg active ingredient. Specific pharmaceutical compositions useful for treatment may comprise about 1 mg, 5 mg, 10 mg, 30 mg, 80 mg, 100 mg, 150 mg, 300 mg and 500 mg of active ingredient.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The utility of the compounds in accordance with the present invention as inhibitors of β-secretase enzyme activity may be demonstrated by methodology known in the art. Enzyme inhibition is determined as follows.

FRET Assay: A homogeneous end point fluorescence resonance energy transfer (FRET) assay is employed with the substrate ([TAMRA-5-CO-EEISEVNLDAEF-NHQSY] QFRET), which is cleaved by BACE 1 to release the fluorescence from TAMRA. The Km of the substrate is not determined due to the limit of solubility of the substrate. A typical reaction contains approximately 30 nM enzyme, 1.25 µM of the substrate, and buffer (50 mM NaOAc, pH 4.5, 0.1 mg/ml BSA, 0.2% CHAPS, 15 mM EDTA and 1 mM deferoxamine) in a total reaction volume of 100 µl. The reaction is proceeded for 30 min and the liberation of TAMRA fragment is measured in a 96-well plate LJL Analyst AD using an excitation wavelength of 530 nm and an emission wavelength of 580 nm. Under these conditions, less than 10% of substrate is processed by BACE 1. The enzyme used in these studies was soluble (transmembrane domain and cytoplasmic extension excluded) human protein produced in a baculovirus expression system. To measure the inhibitory potency of compounds, solutions of inhibitor in DMSO (four concentrations of the inhibitors were prepared: 1 mM, 100 µM, 10 µM, 1 µM) were included in the reactions mixture (final DMSO concentration is 0.8%). All experiments were conducted at room temperature using the standard reaction conditions described above. To determine the $IC_{50}$ of the compound, competitive equation V0/Vi=1+ [I]/[IC50] was used to predict the inhibitory potency of the compounds. The errors in reproducing the dissociation constants are typically less than two-fold.

HPLC assay: A homogeneous end point HPLC assay is employed with the substrate (coumarin-CO-REVNFE-VEFR), which is cleaved by BACE 1 to release the N-terminal fragment attached with coumarin. The Km of the substrate is greater than 100 µM and can not be determined due to the limit of solubility of the substrate. A typical reaction contains approximately 2 nM enzyme, 1.0 µM of the substrate, and buffer (50 mM NaOAc, pH 4.5, 0.1 mg/ml BSA, 0.2% CHAPS, 15 mM EDTA and 1 mM deferoxamine) in a total reaction volume of 100 µl. The reaction is proceeded for 30 min and the reaction is stopped by the addition of 25 µL of 1 M Tris-HCl, pH 8.0. The resulting reaction mixture was loaded on the HPLC and the product was separated from substrate with 5 min linear gradient. Under these conditions, less than 10% of substrate is processed by BACE 1. The enzyme used in these studies was soluble (transmembrane domain and cytoplasmic extension excluded) human protein produced in a baculovirus expression system. To measure the inhibitory potency for compounds, solutions of inhibitor in DMSO (12 concentrations of the inhibitors were prepared and the concentration rage was dependent on the potency predicted by FRET) were included in the reaction mixture (final DMSO concentration is 10%). All experiments were conducted at room temperature using the standard reaction conditions described above. To determine the $IC_{50}$ of the compound, four parameters equation is employed for curve fitting. The errors in reproducing the dissociation constants are typically less than two-fold.

In particular, the compounds of the following examples had activity in inhibiting the beta-secretase enzyme in the aforementioned assay, generally with an $IC_{50}$ from about 1 nM to 1 µM. Such a result is indicative of the intrinsic activity of the compounds in use as inhibitors the beta-secretase enzyme activity.

Several methods for preparing the compounds of this invention are illustrated in the following Schemes and Examples. Starting materials are made according to procedures known in the art or as illustrated herein. The following examples are provided so that the invention might be more fully understood. These examples are illustrative only and should not be construed as limiting the invention in any way.

INTERMEDIATE I

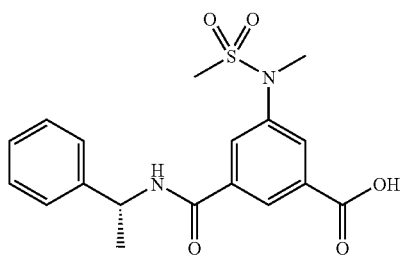

Step A. To a stirred slurry of dimethyl 5-aminoisophthalate (5.0 g, 23.90 mmol) in 100 mL $CH_2Cl_2$/pyridine (3:1) at 0° C. was added methanesulfonyl chloride (1.85 mL, 23.90 mmol). The resulting mixture was stirred for 4 h at room temperature. The solvent was removed in vacuo and ethylacetate (100 mL) was added resulting in precipitate formation. The product was collected by filtration to give the sulfonamide as a white solid. $^1$H NMR (DMSO $_{d6}$) δ 8.15 (s, 1H), 8.02 (s, 2H), 3.89 (s, 6H), 3.02 (s, 3H) LCMS [M–OCH$_3$]$^+$=256.16.

Step B. To a solution of sodium hydride (0153 g, 3.83 mmol, 60% oil dispersion) in 10 mL DMF was added sulfonamide (1.0 g, 3.48 mmol) from step A followed by methyl iodide (0.43 mL, 6.97 mmol). After 1 hr the reaction was quenched with $H_2O$ (100 mL) and extracted with EtOAc (3×50 mL). The organic extracts were dried over $MgSO_4$ and evaporated to give the product. $^1$H NMR (DMSO $_{d6}$) δ 8.40 (s, 1H), 8.19 (s, 2H), 3.91 (s, 6H), 3.34 (s, 3H), 3.01 (s, 3H). LCMS [M+H]=

Step C. Diester (1.03 g, 3.38 mmol) from step B was dissolved in 50 mL THF:MeOH (1:1) and cooled to 0° C. 1N NaOH (3.38 mL, 3.38 mmol) was added and the reaction was allowed to warm to rt over 8 hours. The solution was acidified with 1N HCl (30 mL) and extracted with EtOAc (3×50 mL). The combined organic extracts were washed with brine and dried over $MgSO_4$, filtered and concentrated in vacuo. Purification on silica gel (5% MeOH/CHCl$_3$ containing 1% HOAc) gave the mono acid. $^1$H NMR (DMSO $_{d6}$) δ 8.30 (s, 1H), 8.10 (s, 21H), 3.84 (s, 3H), 3.27 (s, 3H), 2.94 (s, 3H). LCMS (M+H)=288.16.

Step D. A solution containing 0.133 g (0.46 mmol) of the monoacid from step C in 5 mL $CH_2Cl_2$, BOP reagent (0.235 g, 0.55 mmol), (R)-(+)-α-methylbenylamine (0.071 mL, 0.55 mmol), and diisopropylamine (0.24 mL, 1.39 mmol) was stirred at ambient temperature for 1 h. Evaporation of the solvent and column chromatography on silica gel (90% EtOAc/Hexanes) afforded the benzyl amide. $^1$H NMR (CDCl$_3$) δ 8.26 (s, 1H), 8.17 (s, 1H), 8.06 (s, 1H), 7.31 (m, 5H), 6.50 (d, J=7.1 Hz, 1H), 5.33 (q, J=7.1 Hz, 111), 3.96 (s, 3H), 3.37 (s, 3H), 2.88 (s, 3H), 1.64 (d, J=7.0 Hz, 3H). LCMS (M+H)=391.20.

Step E. To 0.171 g (0.438 mmol) of the benzyl amide from step D in 10 mL THF:MeOH (1:1) was added 2 N NaOH (0.66 mL, 1.32 mmol). The solution was heated to 50° C. for 1 h. After cooling the solution was acidified by the addition of 1 N HCl (20 mL) and extracted with EtOAc (3×30 mL). The combined organic extracts were dried over $MgSO_4$, filtered, and concentrated in vacuo to yield the desired carboxylic acid. $^1$H NMR (CDCl$_3$) δ 8.22 (t, 1H), 8.11 (m, 1H), 8.06 (m, 1H), 7.34 (m, 5H), 6.47 (d, J=7.1 Hz, 1H), 5.33 (m, 1H), 3.37 (s, 3H), 2.87 (s, 3H), 1.64 (d, J=7.0 Hz, 3H). LCMS (M+H)=377.2.

INTERMEDIATE II

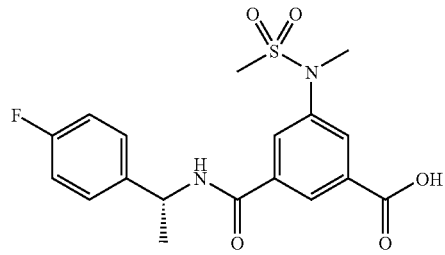

This carboxylic acid was prepared in the same manner as in intermediate I but using (R)-4-fluoro-α-methylbenzyl amine as the amine in step D.

INTERMEDIATE III

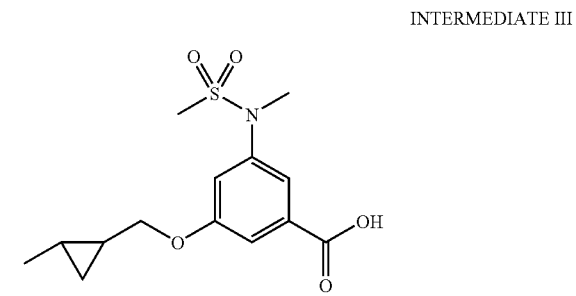

Step A. To a stirred solution of dimethyl 5-hydroxyisophthalate (8.6 g, 41.1 mmol) in 200 mL of acetone was added $K_2CO_3$ (5.7 g, 41.1 mmol) and trans-crotyl bromide (5.5 g, 41.1 mmol). The resulting mixture was stirred at reflux for 16 h. The solids were removed by filtration and the filtrate was evaporated to near dryness. The resulting residue was dissolved in 200 mL of ether and washed 3×20 mL of 1N HCl then brine. The organic extracts were dried over $MgSO_4$ and evaporated to give aryl ether A. $^1$H NMR (CDCl3) δ 8.25 (s, 1H), 7.75 (s, 2H), 5.93 (m, 1H), 5.77 (m, 1H), 4.58 (d, J=2.2 Hz, 2H), 3.91 (s, 6H), 1.81 (d, J=2.2 Hz, 3H). LCMS (M+H)=265.24.

Step B. A 0° C. solution containing 9.4 g (35.6 mmol) of the isophthalate from step A in 300 mL of a 1:1 mixture of THF and MeOH was treated with 35.6 mL (35.6 mmol) of 1N NaOH. The ice bath was allowed to stir to ambient temperature over 16 h. The reaction mixture was concentrated to ca. ⅛ volume before it was acidified with 25 mL of 3N HCl. The solids that precipitated were redissolved in 300 mL of EtOAc and washed with brine (2×25 mL). The organic extract was dried over $MgSO_4$ and evaporated to give the desired carboxylic acid. $^1$H NMR (CDCl3) δ 8.37 (s, 1H), 7.82 (s, 2H), 5.93 1H), 5.77 (m, 1H), 4.58 (d, J=2.2 Hz, 2H), 3.95 (s, 3H), 1.77 (d, J=2.2 Hz, 252.18.

Step C. To a 0° C. solution containing 4.0 g (16.0 mmol) of carboxylic acid III-C in 80 mL of THF was added 4.2 mL (30.2 mmol) of $Et_3N$ and 2.2 mL (22.7 mmol) of ethyl chloroformate. The resulting slurry was stirred for 1 h and treated with 2.46 g (37.8 mmol) of $NaN_3$ dissolved in 15 mL of water. After an additional hour at rt the reaction mixture was diluted with 50 mL of water and washed toluene (3×50 mL). The combined organic extracts were dried over $MgSO_4$ and refluxed over 16 h. The reaction was cooled to rt and treated with 3.1 mL (30.2 mmol) of benzyl alcohol and 4.2 mL (30.2 mmol) of triethylamine. The reaction was refluxed for 24 h, cooled and diluted with 100 mL of EtOAc and 35 mL of 10% citric acid. The organic extract was washed with water and brine then dried over $MgSO_4$. Column chromatograhy (2:3 EtOAc/Hexanes) afforded the carbamate C. $^1$H NMR (CDCl$_3$) δ 7.38 (m, 8H), 6.85 (bs, 1H), 5.85 (m, 1H), 5.65 (m, 1H), 5.20 (s, 2H), 4.44 (d, J=6.0 3H). LCMS (M+H)=356.25.

Step D. A solution of 3.56 g (10.0 mmol) of the aryl ether from step C was dissolved in 100 mL of EtOAc and treated with 50 mL (c.a. 0.5 M, 25 mmol) of freshly prepared $CH_2N_2$. After stirring for 5 minutes, 112 mg (0.5 mmol) of $Pd(OAc)_2$ was added to effect vigorous release of $N_2$. After an additional 30 minutes, the brown slurry was evaporated and chromatographed (1:1 EtOAc/Hexanes) to give the desired cyclopropylmethyl ether. $^1$H NMR (CDCl$_3$) δ 7.55 (s, 1H), 7.44 (m, 7H), 6.80 (bs, 1H), 5.23 (s, 2H), 3.85 (s, 3H), 3.80 (m, 2H), 1.04 (d, 3H), 0.94 (m, 1H), 0.75 (m, 1H), 0.47 (m, 1H), 0.38 (m, 1H). LCMS (M+H)=368.26.

Step E. To a solution of the benzyl carbamate (3.6 g, 10.0 mmol) from step D and 1.5 g of 10% Pd/C in EtOAc (100 mL) was stirred at room temperature under a balloon of hydrogen gas for 5 h. The mixture was filtered through a pad of Celite, concentrated, and purified on silica gel (50% EtOAc/Hexanes) to afford the desired aniline. $^1$H NMR (CDCl$_3$) δ 6.99 (s, 2H), 6.40 (s, 1H), 3.85 (s, 3H), 3.75 (m, 2H), 1.77 (m, 1H), 1.45 (m, 1H), 1.04 (d, 3H), 0.47 (m, 1H), 0.33 (m, 1H). LCMS (M+H)=236.2.

Step F. To a 0° C. solution of the aniline from step E (940 mg, 4.0 mmol) in 30 mL of $CH_2Cl_2$ and of pyridine was added methanesulfonyl chloride (0.40 mL, 4.0 mmol). The resulting mixture was stirred at this temperature for 2 h before being diluted with 100 mL of DCM. The solution was washed with 1N HCl (3×25 mL), water (2×25 mL), and brine (25 mL). The organic phase was dried and concentrated to provide sulfonamide F that was used in the next step without further purification. LCMS (M+H)=314.1.

Step G. The sulfonamide from step F (1.25 g, 4.0 mmol) in DMF (20 in L) was treated with 95% sodium hydride (106 mg, 4.4 mmol) and excess methyl iodide (3 mL). The resulting mixture was stirred at ambient temperature for 1 h and was diluted with 200 mL of ether. The solution was washed with water (7×25 mL) and brine then dried over $MgSO_4$. Purification by silica gel chromatography (2:3 EtOAc/Hexanes) afforded the desired methylated sulfonamide. $^1$H NMR (CDCl$_3$ w/0.05% DMSO-d6) δ 7.65 (s, 1H), 7.41 (s, 1H), 7.15 (s, 1H), 3.93 (s, 3H), 3.80 (t, 2H), 3.30 (S, 3H), 2.87 (s, 3H), 1.11 (d, 3H), 0.88 (m, 1H), 0.55 (m, 1H), 0.37 (m, 1H). LCMS (M+H)=328.23.

Step H. To a stirred solution of the ester from step G (625 mg, 2.0 mmol) in 12 mL THF/MeOH (1:1) was added 15% NaOH (2.2 mL, 8.0 mmol). After the reaction mixture was stirred at 45° C. for 2 h the solvents were evaporated and the residue was acidified with 3N HCl (4.0 mL, 12 mmol). The solid was taken up in 75 mL of DCM and the organic phase was washed with brine. The organic phase was dried and evaporated to yield the desired carboxylic acid as a white solid. $^1$H NMR (CDCl$_3$ w/0.05% DMSO-d6) δ 7.61 (s, 1H), 7.44 (s, 1H), 7.15 (s, 1H), 3.83 (t, 2H), 3.32 (S, 3H), (m, 1H), 0.55 (m, 1H), 0.37 (m, 1H). LCMS (M+H)=314.22.

INTERMEDIATE IV

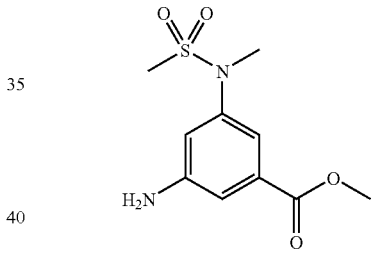

Step A: To 3-amino-5-nitro benzoic acid (3.60 g, 19.78 mmol) in 100 mL MeOH was added thionyl chloride (2.59 g, 21.76 mmol). The solution was heated to 65° C. for 12 h. Concentration in vacuo afforded the methyl ester hydrochloride salt. $^1$H NMR (CD$_3$OD) δ 8.62 (s, 1H), 8.28 (s, 1H), 8.19 (s, 1H), 3.99 (s, 3H).

Step B: To a solution of 3.53 g (18.0 mmol) amino ester from step A in 100 mL $CH_2Cl_2$/pyridine (3:1) was added methanesulfonyl chloride (2.07 g, 18.0 mmol). The reaction was stirred at ambient temperature for 1 h followed by evaporation of the solvent. The gummy residue was taken up in EtOAc (100 mL), acidified with 1N HCl (100 mL), and extracted with EtOAc (3×100 mL). The combined organic extracts were dried over $MgSO_4$, filtered, and concentrated in vacuo to give the sulfonamide as an off-white solid. $^1$H NMR (CD$_3$OD) δ 8.46 (s, 1H), 8.30 (s, 1H), 8.18 (s, 1H), 3.97 (s, 3H), 3.09 (s, 3H).

Step C: Sodium Hydride (0.26 g, 6.55 mmol, 60% oil dispersion) was suspended in 10 mL DMF to which 1.5 g (5.45 mmol) of the sulfonamide from step B (in 10 mL DMF) was added followed by 0.93 g (6.55 mL) methyl iodide. The solution was stirred at ambient temperature for 3 h. The reaction was quenched with $H_2O$ (250 mL), extracted with EtOAc (3×200 mL), dried over MgSO₄, filtered and concentrated in vacuo. Purification by silica gel chromatography provided the N-methyl sulfonamide. LCMS (M–H₂O)=272.2.

Step D. To a solution of the nitro sulfonamide (2.7 g, mmol) from step C and 0.15 g of 10% Pd/C in 50 mL EtOH containing HOAc (2 mL) was stirred at room temperature under a balloon of hydrogen gas for 12 h. The mixture was filtered through a pad of Celite, concentrated, and purified on silica gel (100% EtOAc) to afford the desired aniline. ¹H NMR (CD₃OD) δ 7.29 (s, 1H), 7.26 (s, 1H), 6.95 (s, 1H), 3.87 (s, 3H), 3.27 (s, 3H), 2.89 (s, 3H). LCMS (M+H)= 258.2.

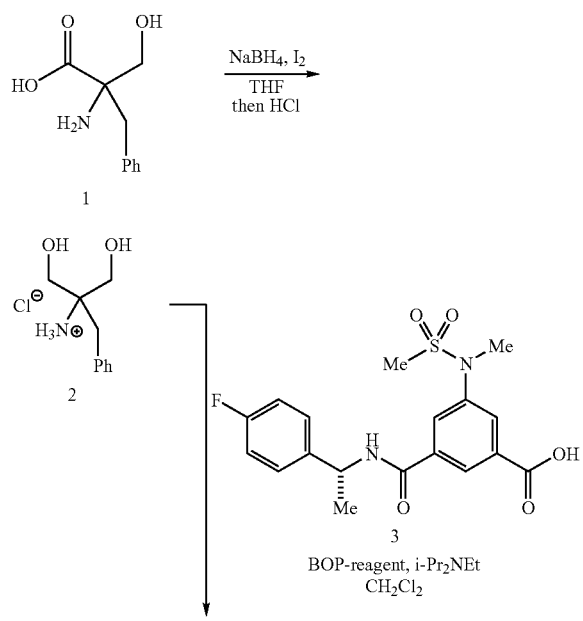

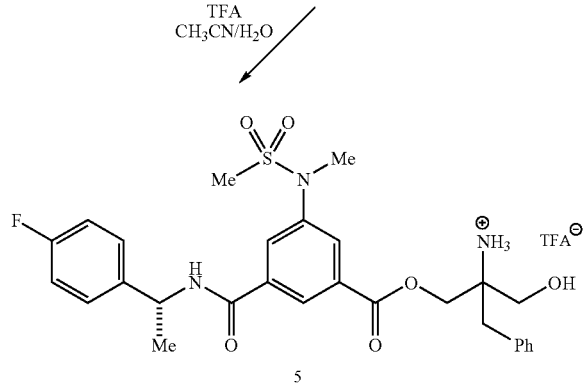

EXAMPLE 1

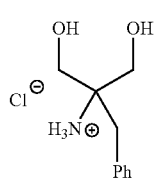

2-Benzyl-1,3-dihydroxypronan-2-ammonium chloride

To a solution of rac-benzylserine (1) (0.40 g, 2.049 mmol) in 6 mL THF at rt was added NaBH₄ (0.271 g 7.171 mmol) in one portion. The solution was fitted with a reflux condenser and cooled to 0° C. Iodine (0.78 g, 3.073 mmol) in 2 mL THF was added dropwise via cannula. After the addition was complete, the reaction was heated to reflux for 15 h. The reaction was then cooled to 0° C. and quenched by the addition of methanol until the bubbling subsided. The residue was acidified by the addition of 6N HCl until the pH was below one, then concentrated to afford the desired product 2 contaminated with various inorganic residue (Redissolving the unpurified reaction mixture in methanol and filtering through a pad of celite, with copious fresh methanol rinses removed some of the undesired inorganic residue). This mixture was used without further purification. ¹H NMR (400 MHz, d₄-MeOH) δ 7.341-7.250 (m, 5H), 3.515 (s, 4H), 2.998 (s, 2H).

EXAMPLE 2

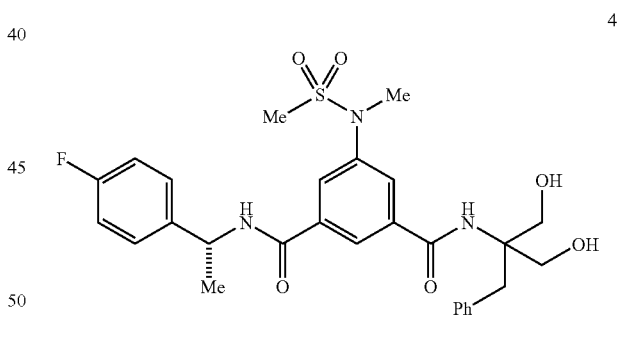

N-[1-Benzyl-2-hydroxy-1-(hydroxymethyl)ethyl]-N'-{[(1R)-1-(4-fluorophenyl)ethyl]-5-} isophthalimide To a slurry of amine hydrochloride 2 (0.442 g, 2.2028 mmol) and acid 3 (0.100 g, 0.254 mmol; Intermediate III) in 3 mL CH₂Cl₂ was added diisopropylethylamine (0.180 mL, 1.014 mmol), followed by BOP-reagent (0.168 g, 0.380 mmol). After 2.5 h, additional diisopropylethylamine (0.90 mL, 0.501 mmol) and BOP-reagent (0.085 g, 0.190 mmol) was added. After 45 min, the reaction was concentrated, redissolved in 2 mL DMF and 0.25 mL H₂O, then purified by reverse-phase preparative HPLC. The mildly acidic fractions containing desired amide 4 were concentrated by lyophilization. ¹H NMR (400 MHz, d₄-MeOH) δ 8.830 (d, J=7.1 Hz, 1H), 8.047 (m, 1H), 7.969 (m, 1H), 7.419-7.254 (m, 3H), 7.238-7.150 (m, 4H), 7.065-7.020 (m, 2H), 5.217 (m, 1H), 3.849 (d, J=9.7 Hz, 2H), 3.732 (d, J=9.7 Hz, 1H), 3.335 (s, 3H), 3.168 (s, 2H), 2.939 (s, 3H), 1.551 (d, J=6.9 Hz, 3H). Low res. MS (ES) M+H=558.

EXAMPLE 3

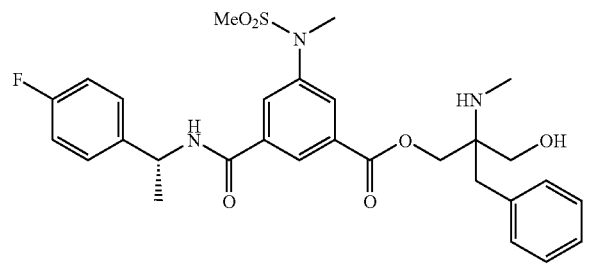

2-Amino-2-benzyl-3-hydroxypropyl-3-({[(1R)-1-(4-fluorophenyl)ethyl]amino}-carbonyl)-5-[methyl(methylsulfonyl)amino]benzoate To a solution of amide 4 (19.2 mg, 0.0344 mmol) in 2 mL CH₃CN and 0.4 mL H₂O was added trifluroacetic acid (0.14 mL). The reaction was allowed to proceed at rt for 14 h, then warmed to 45° C. for 7 h. A further aliquot of trifluoroacetic acid (0.050 mL) was added, and the reaction was maintained at 45° C. for 14 h. The reaction was concentrated, the residue was dissolved in 1 mL DMF, then purified by reverse-phase preparative HPLC to afford the desired ester 5 as a 1:1 mixture of diastereomers. Diastereomer A: ¹H NMR (400 MHz, d₄-MeOH,) δ 9.058 (br s, 1H), 8.425 (m, 1H), 8.260 (m, 1H), 8.136 (m, 1H), 7.438-7.403 (m, 2H), 7.355-7.247 (m, 5H), 7.068-7.020 (m, 2H), 5.246 (m, 1H), 4.469 (d, J=12.1 Hz, 1H), 4.319 (d, J=12.3 Hz, 1H), 3.700 (s, 2H), 3.386 (s, 3H), 3.140 (m, 2H), 2.964 (s, 3H), 1.576 (d, J=7.1 Hz). Diastereomer B: ¹H NMR (400 MHz, d₄-MeOH,) δ 9.038 (br s, 1H) 8.400 (m, 1H), 8.260 (m, 1H), 8.136 (m, 1H), 7.438-7.403 (m, 2H), 7.355-7.247 (m, 5H), 7.068-7.020 (m, 2H) 5.246 (m, 1H), 4.469 (d, J=12.1 Hz, 1H), 4.309 (d, J=12.1 Hz, 1H), 3.700 (s, 2H), 3.386 (s, 3H), 3.140 (m, 2H), 2.964 (s, 3H), 1.576 (d, J=7.1 Hz). Low res. MS (ES) M+H=558.

The following compounds are prepared in a manner similar to the compounds of the foregoing examples using appropriate starting materials and reagents.

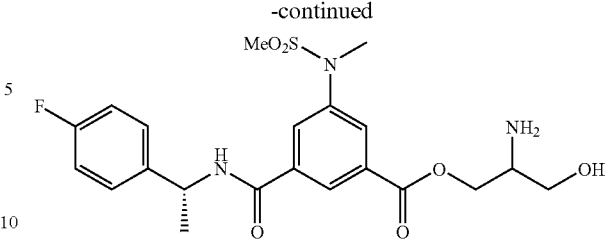

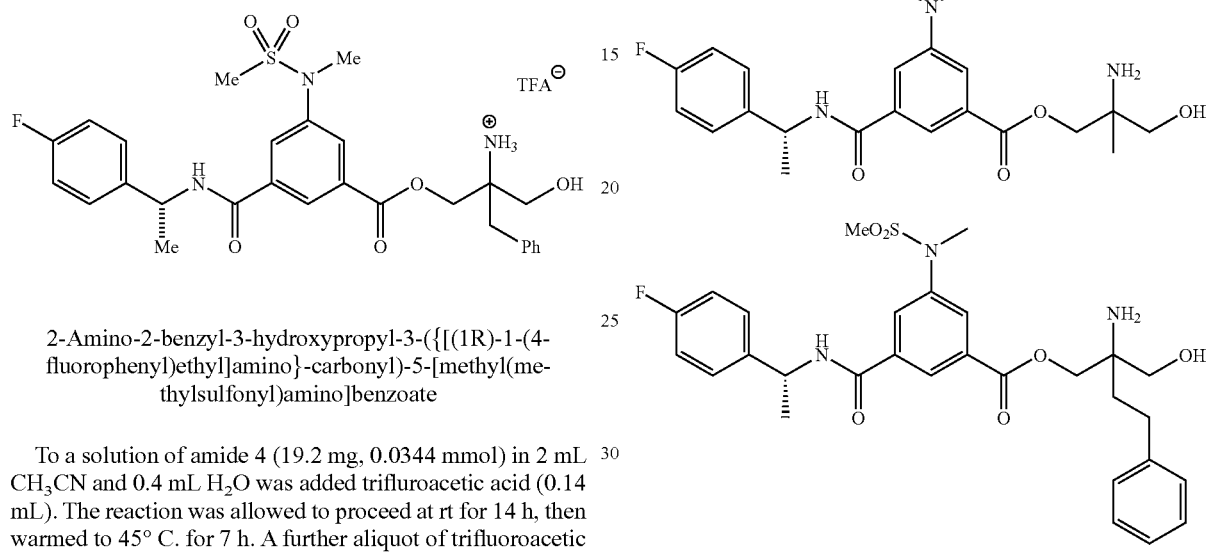

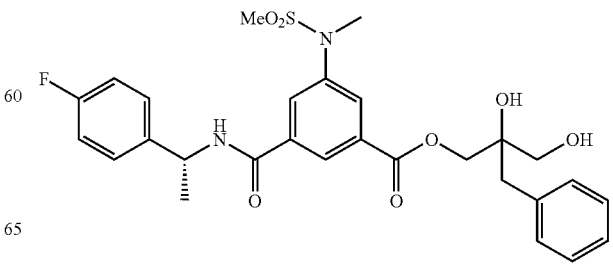

-continued

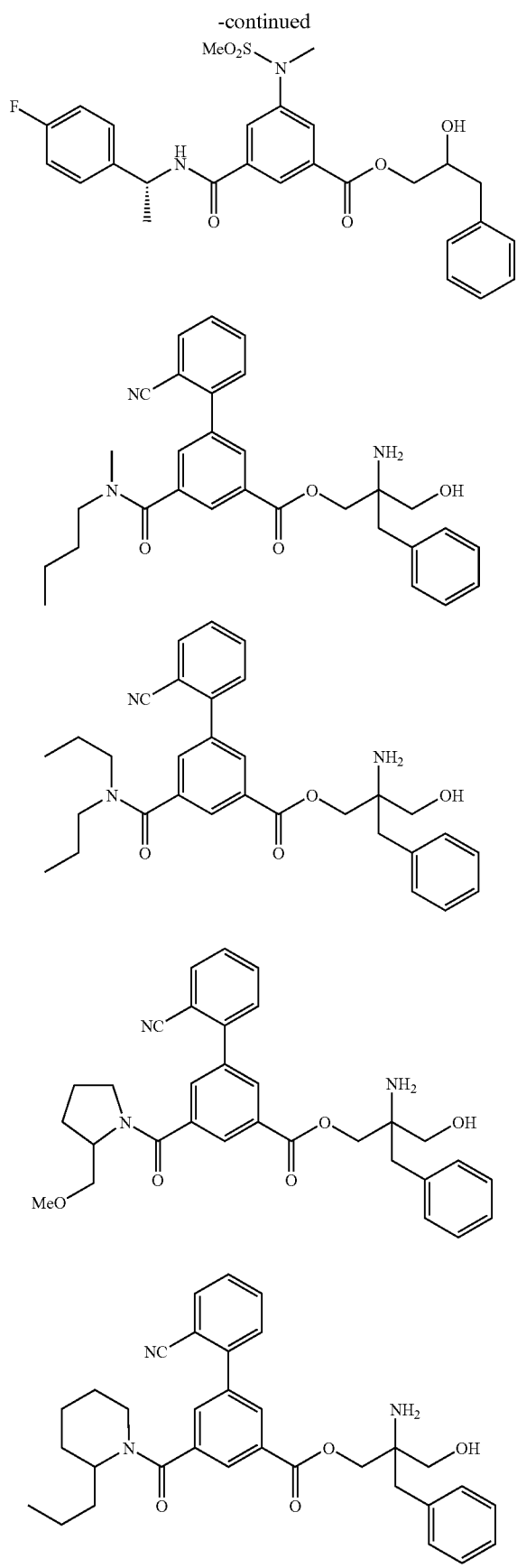

-continued

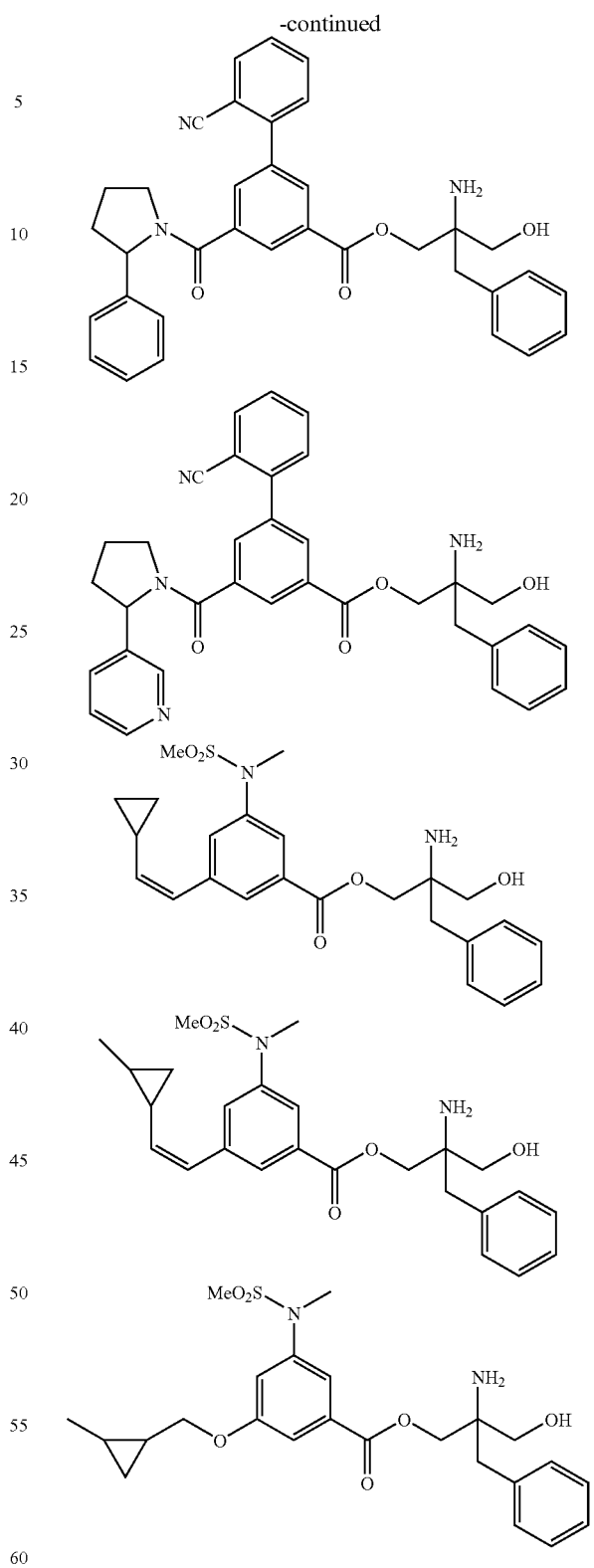

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is

What is claimed is:

1. A compound of the formula I:

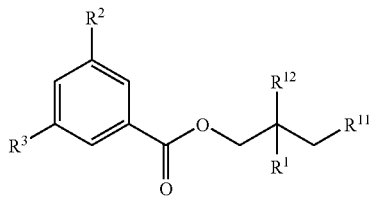

I wherein:
$R^1$ is selected from the group consisting of:
(1) —$C_{1-6}$alkyl,
(2) —$C_{2-6}$ alkenyl,
(3) —$C_{2-6}$ alkynyl,
wherein said alkyl, alkenyl and alkynyl is unsubstituted or substituted with phenyl, which is unsubstituted or substituted with a group selected from:
(i) halo,
(ii) —$C_{1-6}$alkyl,
(iii) —$C_{2-6}$ alkenyl,
(iv) —$C_{2-6}$ alkynyl,
(v) —OH, and
(vi) —O—$C_{1-6}$alkyl,
(4) hydrogen;
$R^2$ is selected from the group consisting of:
(1) ($R^4$—S(O)$_2$N($R^7$)—,
wherein $R^4$ is independently selected from the group consisting of:
(a) —$C_6$alkyl,
(b) —$C_{2-6}$ alkenyl,
(c) —$C_{2-6}$ alkynyl,
wherein said alkyl, alkenyl and alkynyl is unsubstituted or substituted with one to six fluorus,
(d) phenyl, and
(e) benzyl,
wherein $R^7$ is independently selected from the group consisting of:
(a) hydrogen,
(b) —$C_{1-6}$alkyl,
(c) —$C_{2-6}$ alkenyl,
(d) —$C_{2-6}$ alkynyl,
(2)

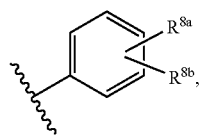

wherein $R^{8a}$ and $R^{8b}$ are independently selected from the group consisting of:
(a) hydrogen,
(b) —CN,
(c) halo,
(d) —$C_{1-6}$alkyl,
(e) —$C_{2-6}$ alkenyl, and
(f) —$C_{2-6}$ alkynyl $R^3$ is selected from the group consisting of:

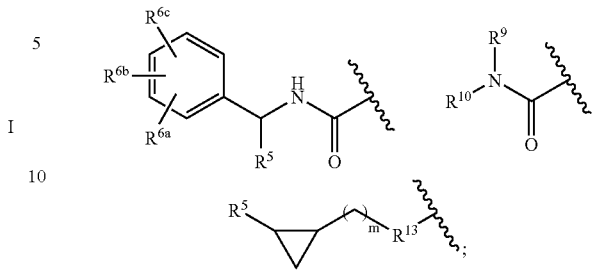

$R^{6a}$, $R^{6b}$, and $R^{6c}$ are independently selected from the group consisting of:
(1) hydrogen, and
(2) halogen;
$R^5$ is selected from the group consisting of:
(1) —$C_{1-6}$alkyl,
(2) —$C_{2-6}$ alkenyl,
(3) —$C_{2-6}$ alkynyl,
wherein said alkyl, alkenyl and alkynyl is unsubstituted or substituted with phenyl, and
(4) hydrogen;
$R^{13}$ is selected from the group consisting of —CH=CH— and —O—;
$R^9$ and $R^{10}$ are independently selected from the group consisting of:
(1) hydrogen,
(2) $C_{1-6}$alkyl,
(3) $C_{2-6}$ alkenyl,
(4) $C_{2-6}$ alkynyl, wherein said alkyl, alkenyl and alkynyl is unsubstituted or substituted with phenyl,
or $R^9$ and $R^{10}$ may be joined together to form a pyrrolidine or piperidine ring which is unsubstituted or substituted with —$C_{1-6}$alkyl, —$C_{2-6}$ alkenyl, —$C_{2-6}$ alkynyl, —$C_{1-6}$alkyl—O—$C_{1-6}$alkyl, phenyl or pyridyl;
$R^{11}$ is selected from the group consisting of:
(1) —OH,
(2) —O—$C_{1-6}$alkyl,
(3) —O—$C_{l-6}$alkyl-phenyl,
(4) —O—phenyl, and
(5) phenyl;
$R^{12}$ is selected from the group consisting of:
(1) —NR$^9$R$^{10}$, and
(2) —OH;
m is independently 0, 1, or 2;
and pharmaceutically acceptable salts thereof.

2. The compound of claim 1 of the formula II:

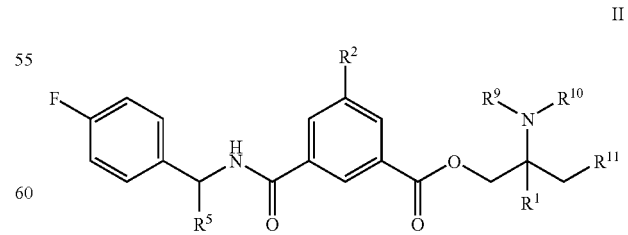

II wherein:
$R^1$ is selected from the group consisting of:
(1) $C_{1-6}$alkyl, unsubstituted or substituted with phenyl, and
(2) hydrogen;

$R^2$ is selected from the group consisting of:
  (1) $R^4$—$S(O)_2N(R^7)$—,
    wherein $R^4$ is independently selected from the group consisting of:
      (a) $C_{1-6}$alkyl, which is unsubstituted or substituted with 1-6 fluoro,
      (b) phenyl, and
      (c) benzyl,
    wherein $R^7$ is independently selected from the group consisting of:
      (a) hydrogen, and
      (b) —$C_{1-6}$alkyl,
  (2)

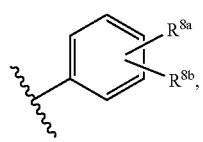

wherein $R^{8a}$ and $R^{8b}$ are independently selected from the group consisting of:
    (a) hydrogen,
    (b) —CN,
    (c) halo, and
    (d) —$C_{1-6}$alkyl,
$R^5$ is selected from the group consisting of:
  (1) $C_{1-6}$alkyl, unsubstituted or substituted with phenyl, and
  (2) hydrogen;
$R^9$ and $R^{10}$ are independently selected from the group consisting of:
  (1) hydrogen, and
  (2) $C_{1-6}$alkyl, unsubstituted or substituted with phenyl;
$R^{11}$ is selected from the group consisting of:
  (1) —OH,
  (2) —O-phenyl, and
  (3) phenyl.

3. The compound of claim 1 of the formula III:

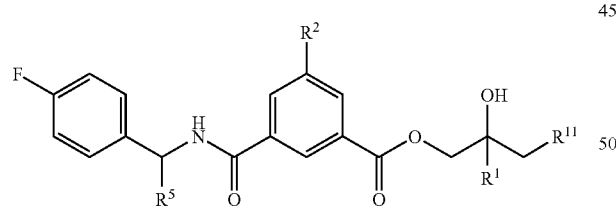

III wherein:
$R^1$ is selected from the group consisting of:
  (1) $C_{1-6}$alkyl, unsubstituted or substituted with phenyl, and
  (2) hydrogen;
$R^2$ is selected from the group consisting of:
  (1) $R^4$—$S(O)_2N(R^7)$—,
    wherein $R^4$ is independently selected from the group consisting of:
      (a) $C_{1-6}$alkyl, which is unsubstituted or substituted with 1-6 fluoro,
      (b) phenyl, and
      (c) benzyl,
    wherein $R^7$ is independently selected from the group consisting of:
      (a) hydrogen, and
      (b) —$C_{1-6}$alkyl,
  (2)

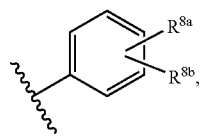

wherein $R^{8a}$ and $R^{8b}$ are independently selected from the group consisting of:
    (a) hydrogen,
    (b) —CN,
    (c) halo, and
    (d) —$C_{1-6}$alkyl,
$R^5$ is selected from the group consisting of:
  (1) $C_{1-6}$alkyl, unsubstituted or substituted with phenyl, and
  (2) hydrogen;
$R^{11}$ is selected from the group consisting of:
  (1) —OH,
  (2) —O-phenyl, and
  (3) phenyl.

4. The compound of claim 1 wherein $R^1$ is selected from the group consisting of:
  (1) benzyl,
  (2) phenyl-ethyl-,
  (3) methyl, and
  (4) hydrogen.

5. The compound of claim 1 wherein $R^2$ is $CH_3$—$S(O)_2$N($CH_3$)—.

6. The compound of claim 1 wherein $R^2$ is cyano-phenyl—.

7. The compound of claim 1 wherein $R^5$ is methyl.

8. The compound of claim 1 wherein $R^9$ and $R^{10}$ are independently selected from the group consisting of:
  (1) hydrogen, and
  (2) methyl.

9. The compound of claim 1 wherein $R^{11}$ is —OH.

10. A compound which is selected from the group consisting of:

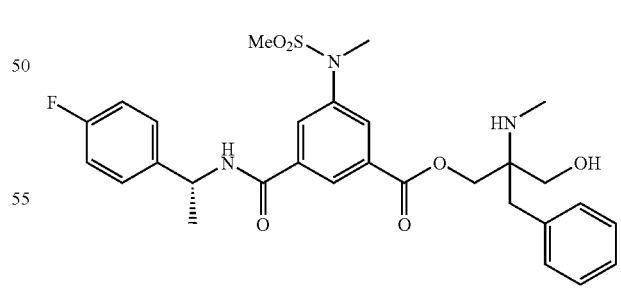

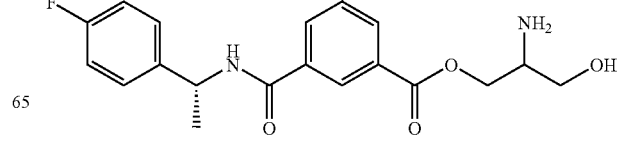

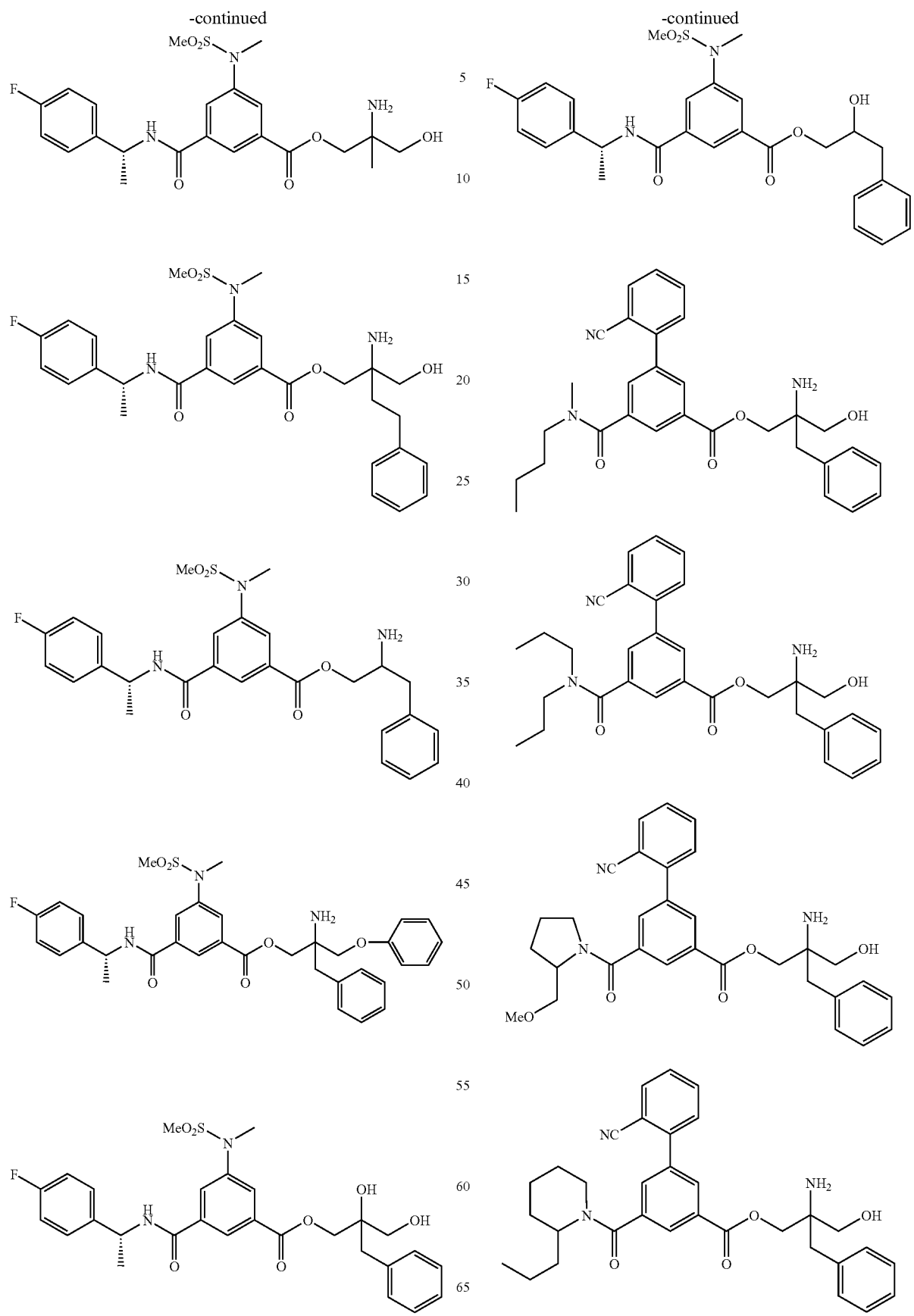

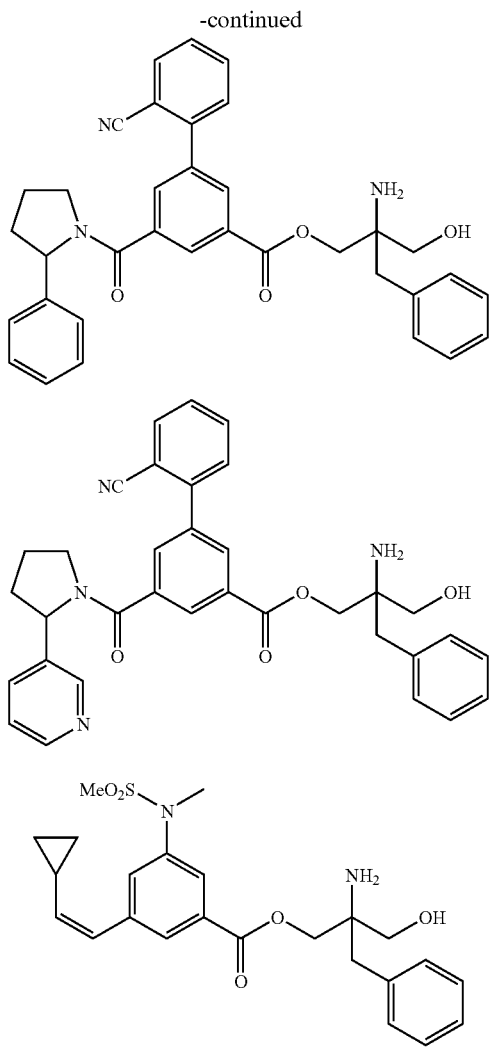
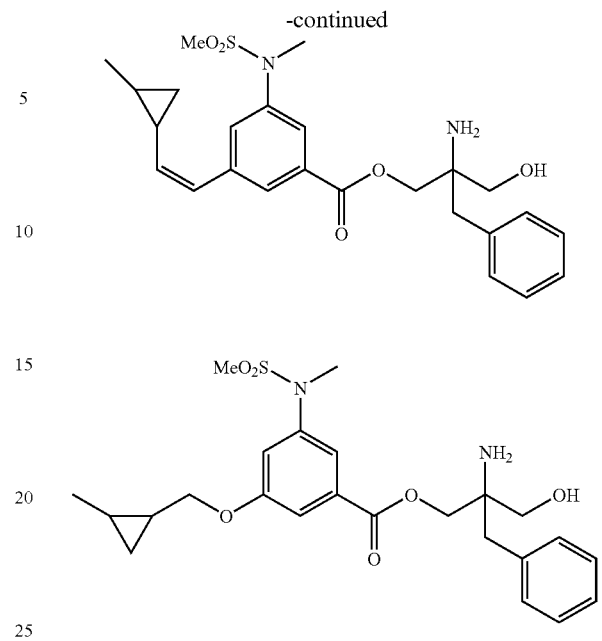

and pharmaceutically acceptable salts thereof.

11. A pharmaceutical composition comprising an effective amount of a compound of claim 1 or a pharmaceutically acceptable salt thereof, and a pharmaceutically acceptable carrier.

12. A method for inhibition of beta-secretase activity in a mammal in need thereof which comprises administering to the mammal a therapeutically effective amount of a compound of claim 1, or a pharmaceutically acceptable salt thereof.

13. A method for treating Alzheimer's disease in a patient in need thereof comprising administering to the patient an effective amount of a compound of claim 1, or a pharmaceutically acceptable salt thereof.

* * * * *